United States Patent [19]
Nakamura

[11] Patent Number: 5,837,135
[45] Date of Patent: Nov. 17, 1998

[54] CHROMATOGRAPHY AND RELATED APPARATUS SYSTEM

[75] Inventor: Susumu Nakamura, Tsuchiura, Japan

[73] Assignee: Agency of Industrial Science and Technology, Japan

[21] Appl. No.: 887,646

[22] Filed: Jul. 3, 1997

[30] Foreign Application Priority Data

Jul. 9, 1996 [JP] Japan ................................. 8-178832

[51] Int. Cl.$^6$ .................................................. B01D 15/08
[52] U.S. Cl. ..................... 210/198.2; 210/656; 73/61.58; 422/70
[58] Field of Search ..................... 210/635, 656, 210/659, 85, 93, 198.2; 73/61.52, 61.58; 422/70; 436/161

[56] References Cited

U.S. PATENT DOCUMENTS 4,988,447  1/1991  Hellinger .................. 210/659
4,990,250  2/1991  Hellinger .................. 210/198.2
5,234,586  8/1993  Afeyan .................. 210/198.2
5,491,096  2/1996  Sportman .................. 436/518

*Primary Examiner*—Ernest G. Therkorn
*Attorney, Agent, or Firm*—Wenderoth, Lind & Ponack

[57] ABSTRACT

Proposed is an improvement in a detection and recording system in the conventional chromatography in which the chromatographic signals are detected by means of a single detector sometimes to cause difficulties in resolution of the signal of minor component masked by the major component or in separation of two components having about the same retention times. The improvement comprises using two or more detectors to generate signals with a phase difference and recording the differential signal between the two signals obtained in the plurality of detectors.

1 Claim, 2 Drawing Sheets

TIME, seconds

TIME, seconds

CHROMATOGRAPHY AND RELATED APPARATUS SYSTEM

BACKGROUND OF THE INVENTION

The present invention relates to an improvement in chromatography including gas chromatography and liquid chromatography and an apparatus system used in such an improved chromatographic method. More particularly, the invention relates to an improvement in a chromatographic method, by which the respective components of the sample can be accurately detected and quantitatively determined, as well as to an apparatus system for such an improved chromatographic method.

As is known, the chromatographic methods are classified into gas chromatography in which an inert gas is used as the mobile phase and liquid chromatography in which an inert solvent is used as the mobile phase. The liquid chromatographic methods are further classified into several types including adsorption chromatography, in which a porous adsorbent such as silica gel, alumina gel and the like is used as the stationary phase on which the solutes are adsorbed followed by elution from the stationary phase by using a solvent as the eluant to cause separation of the respective components by utilizing the difference in the adsorptive strengths thereof, partition chromatography, in which the components of the sample are separated by utilizing the difference in the partition ratios of the respective components between the mobile phase and the stationary phase, ion-exchange chromatography, in which an ion exchanger is used as the stationary phase, gel-permeation chromatography, in which a porous gel is used as the stationary phase, and so on.

In each of these chromatographic methods, analysis of the components is performed by continuously detecting the components transferred into the mobile phase from the stationary phase and recording the signals of an analytical parameter. In the apparatus system for liquid chromatography shown by the block diagram of FIG. 4, for example, the solvent as the eluant is introduced from the eluant reservoir 1 by means of a metering pump 2 into the chromatographic system to carry the sample S introduced into the system at the sample inlet port 3 toward the separation column 4 filled with the stationary phase on which the components in the sample S are adsorbed. Thereafter, the thus adsorbed sample components are eluted out at different rates by the eluant further continuously introduced into the column 4 and the eluate solution containing the successively eluted solutes is passed through the detector 5 where the signals of an analytical parameter corresponding to the amounts of the respective solutes are detected and recorded in the recorder 9 as a function of the elution time.

As is described above, it is conventional in the prior art chromatographic method and chromatographic apparatus system that the analytical parameter for the respective components is detected by using a single detector for the concentration of the solute in the eluate and the signals are recorded as a function of the elution time, from which the chromatographic analysis is performed for the identification of the components and quantitative determination thereof.

In the above described chromatographic system, the signal obtained in the detector and recorded in the recorder is merely a direct indication of the concentration of the solute which naturally varies as a function of the elution time. A serious problem in such a chromatographic system is that the signal of a trace amount of an impurity contained in a high-purity sample is sometimes masked by the large signal of the principal ingredient or the signals of two components having elution times each close to the other naturally overlap not to be resolved into the respective signals so that the analytical results in such cases are not accurate enough.

SUMMARY OF THE INVENTION

The present invention accordingly has an object to provide an improvement in the chromatographic method and apparatus system therefor, by which quite accurate and reliable analytical results can be obtained even for a small signal of a trace component of which the signal is masked by a large signal of the principal component or when two signals are inseparably overlapping.

Thus, the present invention provides an improvement, in a chromatographic method comprising adsorption of sample components on the adsorbent in a separation column, continuous introduction of a mobile phase fluid into the separation column to cause desorption of the components from the adsorbent at different rates, successive detection of the components carried by the mobile phase fluid in a detector unit to generate signals and recording of the signals in a recorder, which comprises performing at least twice of the detection with a phase difference, obtaining a differential signal between the signals of the two detections and recording the differential signal from which the respective components are analyzed.

The present invention further provides an improvement, in a chromatographic apparatus system comprising a reservoir for a mobile phase fluid, mobile phase feeding means, sample-introducing means, adsorption and separation column and detecting means connected in series and recording means to which the signals from the detecting means are inputted to be recorded, which comprises providing, in the detecting means, at least two detectors differentially operating with a phase difference and having a recording means capable of recording a differential signal between the outputs from the detectors in the detecting means.

DETAILED DESCRIPTION OF THE PREFERRED EMBODIMENTS

In the following, the improvement according to the present invention is described in more detail by way of an embodiment making reference to the accompanying drawing.

Figure 1:
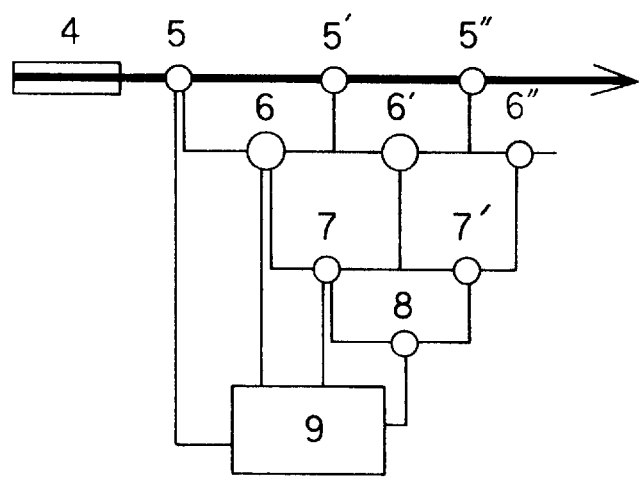
FIG. 1 is a block diagram illustrating the chromatographic apparatus system according to the present invention.

FIG. 1 is a block diagram of the chromatographic apparatus system constructed by using three detectors 5, 5', 5" arranged in series. The components desorbed or eluted out from the adsorbent in the separation column 4 are simultaneously detected in these detectors 5, 5', 5" which output the signals $A^1$, $A^2$, $A^3$ converted, for example, into voltage values. The signals $A^1$ and $A^2$ from the detectors 5 and 5' are outputted with a time lag $\Delta$or, namely, with a phase difference so that the signal $A^2$ outputted at a moment from the second detector 5' is just the same as the signal $A^1$ outputted from the first detector 5 at the moment $\Delta t$ before the moment of the output of the signal $A^2$ from the second detector 5'.

The voltage values of the signals $A^1$ and $A^2$ are processed in a differential amplifier 6 which outputs the differential as a signal $B^1$ which is the first-order differential of the signals $A^1$ and $A^2$. Similarly, the voltage values from the detectors 5' and 5" are processed in the second differential amplifier 6' which outputs the first-order differential $B^2$ of the signals $A^2$ and $A^3$.

In the next place, these first-order differential signals $B^1$ and $B^2$ obtained in the above described manner are processed in another differential amplifier 7 which outputs the second-order differential signal $C^1$. In this way, an n-th-order differential signal of the voltage values can be obtained by means of (n+1) detectors arranged in series and n differential amplifiers in a cascade connection. The final differential voltage signal is recorded in the recorder 9.

The analytical parameter to be detected in the detectors is not particularly limitative so that the detectors conventionally used in chromatographic apparatus system can be used as such in the present invention. Various types of detectors can be used including ultraviolet-visible light detectors, spectrometric infrared detectors, differential refractometers, fluorescence detectors, ultraviolet multiwavelength detectors, electroconductivity detectors, electrochemical detectors, laser detectors, induction-coupling high-frequency plasma-emission detectors, streaming potential detectors and so on. The signals obtained from these detectors are transduced, for example, into voltage signals from which a differential signal can be outputted by means of the above mentioned differential amplifiers.

Excepting for the above described alteration in the detector system, the chromatographic apparatus system according to the present invention can be conventional so that the mobile phase reservoir, mobile phase feed means, sample introducing means, adsorption and separation column and recorder used in the prior art chromatographic systems can be employed here as such. The chromatographic analytical conditions can also be conventional.

In the following, the improvement according to the present invention is described in more detail by way of Examples.

EXAMPLE 1

A liquid chromatographic system was constructed from a metering pump (Model 576, manufactured by GL Science Co.), an injector with a 20 $\mu$loop (Model 7125, a product by Rheodyne Co.), an octadecylsilylated silica gel column of 4.6 mm inner diameter and 50 mm length filled with adsorbent particles of 5 $\mu$m particle diameter and 10 nm pore diameter (a product by Fuji Serial Chemical Co.), two ultraviolet detectors (Model SPD6AV, manufactured by Shimadzu Seisakusho Co.), a differential amplifier and a recorder (Model U228, manufactured by Shimadzu Seisakusho Co.). The differential amplifier, which was assembled by the inventor himself, has a time constant of about 1 ms and is capable of working in a voltage range of 1 mV to 10 V.

Liquid chromatography was performed at room temperature for pure benzene and a benzene mixture containing 25% by weight of an impurity as the samples with a 1:1 by volume mixture of water and acetonitrile as the eluant introduced into the column at a flow rate of 1 ml/minute. Detection of the eluted components was undertaken ultraviolet-spectro-photometrically at a wavelength of 254 nm.

Assuming an impurity component of which the retention time, i.e. the time from introduction of the sample to detection of the signal for the component, longer by 5 seconds than the retention time of benzene, 20 $\mu$l and 5 $\mu$l of a solution of benzene in acetonitrile in a concentration of 100 $\mu$g/ml were introduced into a first sample-inlet port and a second sample-inlet port, respectively, connected in series. The second sample-inlet port was opened at a moment 5 seconds after opening of the first sample-inlet port to obtain a signal of the impurity.

Figure 2A:
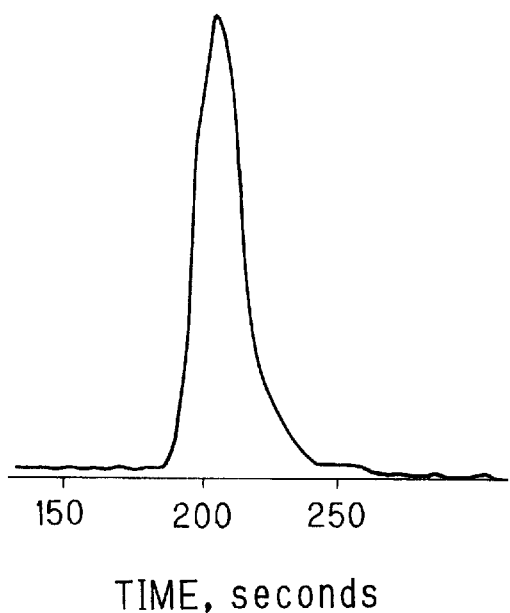
FIGS. 2A and 2B are each a signal recording of pure benzene obtained by the conventional method and by the method according to the invention, respectively.
Figure 2B:
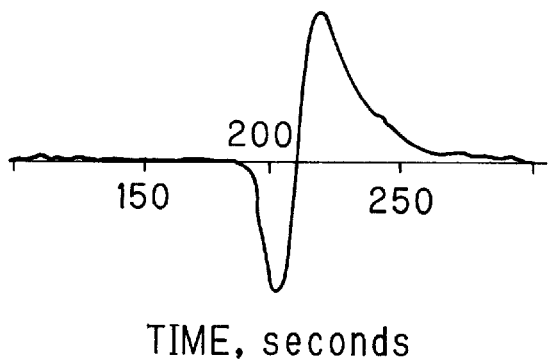

FIG. 2B shows the first-order differential signal of pure benzene obtained in this manner. For comparative purpose, the signal of the same sample was recorded by using a conventional chromatographic system to give the result shown in FIG. 2A. The retention time was about 3 minutes and 30 seconds in each of these chromatographic systems.

Figure 3A:
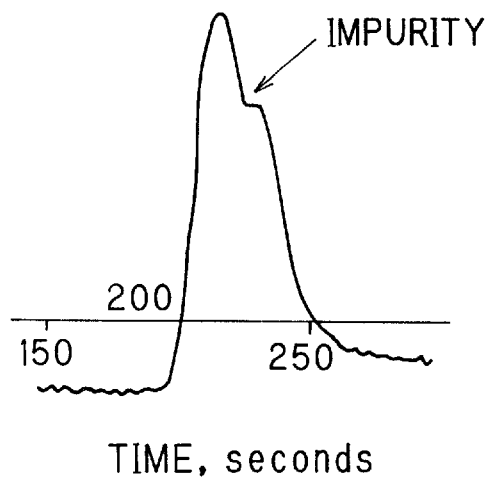
FIGS. 3A and 3B are each a signal recording of benzene containing a small amount of an impurity obtained by the conventional method and by the method according to the invention, respectively.
Figure 3B:
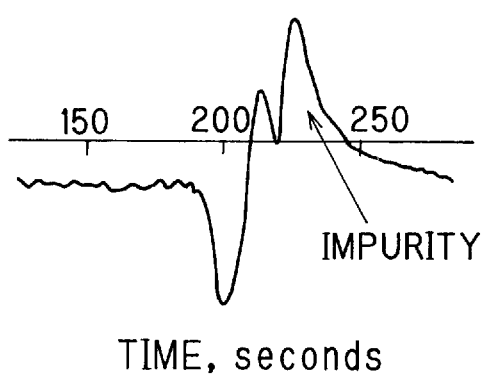
Figure 4:
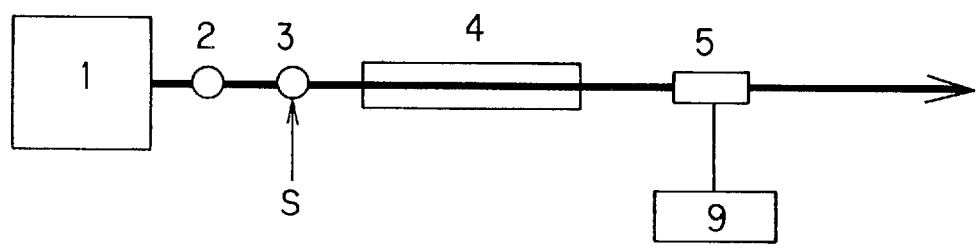
FIG. 4 is a block diagram illustrating the chromatographic apparatus system according to a conventional chromatographic method.

FIG. 3A is a chromatographic recording of the above mentioned impurity-containing benzene taken on a conventional chromatographic system, in which the shoulder signal on the principal peak corresponds to the impurity recorded with a 5 seconds lag of the elution time. FIG. 3B is the first-order differential signal recorded according to the invention for the same impurity-containing benzene, in which the signal corresponding to the impurity can be clearly and definitely isolated from the signal for the principal component.

EXAMPLE 2

The experimental procedure was just the same as in Example 1 described above except that the flow rate of the eluant was increased from 1 ml/minute to 1.5 ml/minute. The results were as satisfactory as in Example 1 except that the retention time was about 2 minutes and 20 seconds instead of about 3 minutes and 30 seconds.

What is claimed is:

1. In a chromatographic apparatus system comprising a reservoir for a mobile phase fluid, mobile phase feeding means, sample-introducing means, adsorption and separation column and detecting means connected in series and a recording means to which the signals from the detecting means are inputted to be recorded, the improvement which comprises providing, in the detecting means, at least two detectors differentially operating with a phase difference and having a recording means capable of recording a differential signal between the outputs from the detectors in the detecting means.

* * * * *